US011185695B1

(12) United States Patent
Osorio et al.

(10) Patent No.: US 11,185,695 B1
(45) Date of Patent: Nov. 30, 2021

(54) METHOD AND SYSTEM FOR LOGGING QUANTITATIVE SEIZURE INFORMATION AND ASSESSING EFFICACY OF THERAPY USING CARDIAC SIGNALS

(75) Inventors: Ivan Osorio, Leawood, KS (US); Mark G. Frei, Lawrence, KS (US)

(73) Assignee: Flint Hills Scientific, L.L.C., Lawrence, KS (US)

( * ) Notice: Subject to any disclaimer, the term of this patent is extended or adjusted under 35 U.S.C. 154(b) by 759 days.

(21) Appl. No.: 12/315,390

(22) Filed: Dec. 3, 2008

Related U.S. Application Data

(62) Division of application No. 10/997,540, filed on Nov. 24, 2004, now Pat. No. 9,050,469.

(60) Provisional application No. 60/525,501, filed on Nov. 26, 2003.

(51) Int. Cl.
*A61N 1/36* (2006.01)

(52) U.S. Cl.
CPC ..... *A61N 1/36064* (2013.01); *A61N 1/36135* (2013.01)

(58) Field of Classification Search
CPC .................. A61N 1/36064; A61N 1/36135
USPC ........ 607/4, 6, 14, 17, 24, 45; 600/483, 485, 600/544
See application file for complete search history.

(56) References Cited

U.S. PATENT DOCUMENTS

| 3,850,161 | A | | 11/1974 | Liss |
| 4,088,138 | A | * | 5/1978 | Diack et al. ...................... 607/6 |
| 4,172,459 | A | | 10/1979 | Hepp |
| 4,291,699 | A | | 9/1981 | Geddes et al. |
| 4,541,432 | A | | 9/1985 | Molina-Negro et al. |
| 4,573,481 | A | | 3/1986 | Bullara |
| 4,702,254 | A | | 10/1987 | Zabara |
| 4,867,164 | A | | 9/1989 | Zabara |
| 4,920,979 | A | | 5/1990 | Bullara |
| 4,949,721 | A | | 8/1990 | Toriu et al. |
| 4,979,511 | A | | 12/1990 | Terry, Jr. |
| 5,025,807 | A | | 6/1991 | Zabara |
| 5,113,869 | A | | 5/1992 | Nappholz et al. |
| 5,137,020 | A | | 8/1992 | Wayne et al. |
| 5,154,172 | A | | 10/1992 | Terry, Jr. et al. |
| 5,156,148 | A | | 10/1992 | Cohen |

(Continued)

FOREIGN PATENT DOCUMENTS

| EP | 1145736 | 10/2001 |
| EP | 1486232 | 12/2004 |

(Continued)

OTHER PUBLICATIONS

Bachman, D.,S. et al.; "*Effects of Vagal Volleys and Serotonin on Units of Cingulate Cortex in Monkeys*;" Brain Research , vol. 130 (1977). pp. 253-269.

(Continued)

*Primary Examiner* — Michael J D Abreu
(74) *Attorney, Agent, or Firm* — CF3; Stephen Eisenmann

(57) ABSTRACT

A system and method for analyzing and logging changes in brain state of a subject for administering therapy to the subject based on the at least one cardiac signal wherein the system and method comprises the steps of receiving at least one cardiac signal of the subject into a processor, analyzing the cardiac signal to detect at least one cardiac signal change indicative of a brain state change, and logging at least one characteristic of the detected signal change or the brain state change.

5 Claims, 3 Drawing Sheets

(56) References Cited

U.S. PATENT DOCUMENTS

| | | | |
|---|---|---|---|
| 5,179,950 | A | 1/1993 | Stanislaw |
| 5,186,170 | A | 2/1993 | Varrichio et al. |
| 5,188,104 | A | 2/1993 | Wernicke et al. |
| 5,188,106 | A | 2/1993 | Nappholz et al. |
| 5,203,326 | A | 4/1993 | Collins |
| 5,205,285 | A | 4/1993 | Baker, Jr. |
| 5,215,086 | A | 6/1993 | Terry, Jr. et al. |
| 5,215,089 | A | 6/1993 | Baker, Jr. |
| 5,222,494 | A | 6/1993 | Baker, Jr. |
| 5,231,988 | A | 8/1993 | Wernicke et al. |
| 5,235,980 | A | 8/1993 | Varrichio et al. |
| 5,237,991 | A | 8/1993 | Baker, Jr. et al. |
| 5,243,980 | A | 9/1993 | Mehra |
| 5,251,634 | A | 10/1993 | Weinberg |
| 5,263,480 | A | 11/1993 | Wernicke et al. |
| 5,269,301 | A | 12/1993 | Cohen |
| 5,269,302 | A * | 12/1993 | Swartz et al. ................. 607/45 |
| 5,269,303 | A | 12/1993 | Wernicke et al. |
| 5,282,474 | A | 2/1994 | Sosa et al. |
| 5,299,569 | A | 4/1994 | Wernicke et al. |
| 5,304,206 | A | 4/1994 | Baker, Jr. et al. |
| 5,311,876 | A | 5/1994 | Olsen et al. |
| 5,313,953 | A | 5/1994 | Yomtov et al. |
| 5,330,505 | A | 7/1994 | Cohen |
| 5,330,507 | A | 7/1994 | Schwartz |
| 5,330,515 | A | 7/1994 | Rutecki et al. |
| 5,334,221 | A | 8/1994 | Bardy |
| 5,335,657 | A | 8/1994 | Terry, Jr. et al. |
| 5,404,877 | A | 4/1995 | Nolan et al. |
| 5,425,373 | A | 6/1995 | Causey, III |
| 5,522,862 | A | 6/1996 | Testerman et al. |
| 5,527,344 | A | 6/1996 | Arzbaecher et al. |
| 5,540,730 | A | 7/1996 | Terry, Jr. et al. |
| 5,540,734 | A | 7/1996 | Zabara |
| 5,571,150 | A | 11/1996 | Wernicke et al. |
| 5,611,350 | A | 3/1997 | John |
| 5,645,570 | A | 7/1997 | Corbucci |
| 5,651,378 | A | 7/1997 | Matheny et al. |
| 5,658,318 | A | 8/1997 | Stroetmann et al. |
| 5,683,422 | A | 11/1997 | Rise et al. |
| 5,690,681 | A | 11/1997 | Geddes et al. |
| 5,690,688 | A | 11/1997 | Noren et al. |
| 5,700,282 | A | 12/1997 | Zabara |
| 5,707,400 | A | 1/1998 | Terry, Jr. et al. |
| 5,716,377 | A | 2/1998 | Rise et al. |
| 5,720,771 | A | 2/1998 | Snell |
| 5,743,860 | A | 4/1998 | Hively et al. |
| 5,792,186 | A | 8/1998 | Rise |
| 5,800,474 | A | 9/1998 | Benabid et al. |
| 5,833,709 | A | 11/1998 | Rise et al. |
| 5,913,876 | A | 6/1999 | Taylor et al. |
| 5,916,239 | A | 6/1999 | Geddes et al. |
| 5,928,272 | A * | 7/1999 | Adkins .............. A61N 1/36135 607/45 |
| 5,941,906 | A | 8/1999 | Barreras, Sr. et al. |
| 5,942,979 | A | 8/1999 | Luppino |
| 5,978,702 | A | 11/1999 | Ward et al. |
| 5,987,352 | A | 11/1999 | Klein et al. |
| 5,995,868 | A * | 11/1999 | Dorfmeister et al. ........ 600/544 |
| 6,016,449 | A | 1/2000 | Fischell et al. |
| 6,018,682 | A | 1/2000 | Rise |
| 6,061,593 | A | 5/2000 | Fischell et al. |
| 6,073,048 | A | 6/2000 | Kieval et al. |
| 6,083,249 | A | 7/2000 | Familoni |
| 6,091,992 | A | 7/2000 | Bourgeois et al. |
| 6,104,956 | A | 8/2000 | Naritoku et al. |
| 6,115,628 | A | 9/2000 | Stadler et al. |
| 6,115,630 | A | 9/2000 | Stadler et al. |
| 6,128,538 | A | 10/2000 | Fischell et al. |
| 6,134,474 | A | 10/2000 | Fischell et al. |
| 6,167,311 | A | 12/2000 | Rezai |
| 6,171,239 | B1 | 1/2001 | Humphrey |
| 6,175,764 | B1 | 1/2001 | Loeb et al. |
| 6,205,359 | B1 | 3/2001 | Boveja |
| 6,208,894 | B1 | 3/2001 | Schulman et al. |
| 6,208,902 | B1 | 3/2001 | Boveja |
| 6,221,908 | B1 | 4/2001 | Kilgard et al. |
| 6,248,080 | B1 | 6/2001 | Miesel et al. |
| 6,253,109 | B1 | 6/2001 | Gielen |
| 6,269,270 | B1 | 7/2001 | Boveja |
| 6,272,379 | B1 | 8/2001 | Fischell et al. |
| 6,304,775 | B1 | 10/2001 | Iasemidis et al. |
| 6,324,421 | B1 | 11/2001 | Stadler et al. |
| 6,337,997 | B1 | 1/2002 | Rise |
| 6,339,725 | B1 | 1/2002 | Naritoku et al. |
| 6,341,236 | B1 | 1/2002 | Osorio et al. |
| 6,356,784 | B1 | 3/2002 | Lozano et al. |
| 6,356,788 | B2 | 3/2002 | Boveja |
| 6,366,813 | B1 | 4/2002 | DiLorenzo |
| 6,366,814 | B1 | 4/2002 | Boveja et al. |
| 6,374,140 | B1 | 4/2002 | Rise |
| 6,397,100 | B2 | 5/2002 | Stadler et al. |
| 6,427,086 | B1 | 7/2002 | Fischell et al. |
| 6,429,217 | B1 | 8/2002 | Puskas |
| 6,449,512 | B1 | 9/2002 | Boveja |
| 6,459,936 | B2 | 10/2002 | Fischell et al. |
| 6,463,328 | B1 | 10/2002 | John |
| 6,466,822 | B1 | 10/2002 | Pless |
| 6,473,639 | B1 | 10/2002 | Fischell et al. |
| 6,473,644 | B1 | 10/2002 | Terry, Jr. et al. |
| 6,477,418 | B2 | 11/2002 | Plicchi et al. |
| 6,480,743 | B1 | 11/2002 | Kirkpatrick et al. |
| 6,484,132 | B1 | 11/2002 | Hively et al. |
| 6,501,983 | B1 | 12/2002 | Natarajan et al. |
| 6,505,074 | B2 | 1/2003 | Boveja et al. |
| 6,532,388 | B1 | 3/2003 | Hill et al. |
| 6,542,774 | B2 | 4/2003 | Hill et al. |
| 6,549,804 | B1 | 4/2003 | Osorio et al. |
| 6,556,868 | B2 | 4/2003 | Naritoku et al. |
| 6,560,486 | B1 | 5/2003 | Osorio et al. |
| 6,564,102 | B1 | 5/2003 | Boveja |
| 6,587,719 | B1 | 7/2003 | Barrett et al. |
| 6,587,727 | B2 | 7/2003 | Osorio et al. |
| 6,594,524 | B2 | 7/2003 | Esteller et al. |
| 6,599,250 | B2 | 7/2003 | Webb et al. |
| 6,609,025 | B2 | 8/2003 | Barrett et al. |
| 6,610,713 | B2 | 8/2003 | Tracey |
| 6,611,715 | B1 | 8/2003 | Boveja |
| 6,615,081 | B1 | 9/2003 | Boveja |
| 6,615,085 | B1 | 9/2003 | Boveja |
| 6,622,038 | B2 | 9/2003 | Barrett et al. |
| 6,622,041 | B2 | 9/2003 | Terry, Jr. et al. |
| 6,622,047 | B2 | 9/2003 | Barrett et al. |
| 6,628,985 | B2 | 9/2003 | Sweeney et al. |
| 6,628,987 | B1 | 9/2003 | Hill et al. |
| 6,647,296 | B2 | 11/2003 | Fischell et al. |
| 6,656,125 | B2 | 12/2003 | Misczynski et al. |
| 6,656,960 | B2 | 12/2003 | Puskas |
| 6,668,191 | B1 | 12/2003 | Boveja |
| 6,671,555 | B2 | 12/2003 | Gielen et al. |
| 6,671,556 | B2 | 12/2003 | Osorio et al. |
| 6,684,105 | B2 | 1/2004 | Cohen et al. |
| 6,721,603 | B2 | 4/2004 | Zabara et al. |
| 6,735,474 | B1 | 5/2004 | Loeb et al. |
| 6,738,671 | B2 | 5/2004 | Christophersom et al. |
| 6,760,626 | B1 | 7/2004 | Boveja |
| 6,768,969 | B1 | 7/2004 | Nikitin et al. |
| 6,788,975 | B1 | 9/2004 | Whitehurst et al. |
| 6,793,670 | B2 | 9/2004 | Osorio et al. |
| 6,819,953 | B2 | 11/2004 | Yonce et al. |
| 6,819,956 | B2 | 11/2004 | DiLorenzo |
| 6,832,114 | B1 | 12/2004 | Whitehurst et al. |
| 6,836,685 | B1 | 12/2004 | Fitz |
| 6,885,888 | B2 | 4/2005 | Rezai |
| 6,904,390 | B2 | 6/2005 | Nikitin et al. |
| 6,920,357 | B2 | 7/2005 | Osorio et al. |
| 6,934,580 | B1 | 8/2005 | Osorio et al. |
| 6,934,585 | B1 | 8/2005 | Schloss |
| 6,944,501 | B1 | 9/2005 | Pless |
| 6,957,107 | B2 | 10/2005 | Rogers |
| 6,961,618 | B2 | 11/2005 | Osorio et al. |
| 6,985,771 | B2 | 1/2006 | Fischell et al. |
| 6,990,377 | B2 | 1/2006 | Gliner et al. |
| 7,006,859 | B1 | 2/2006 | Osorio et al. |

(56) References Cited

U.S. PATENT DOCUMENTS

| | | | |
|---|---|---|---|
| 7,006,872 B2 | 2/2006 | Gielen et al. | |
| 7,010,351 B2 | 3/2006 | Firlik et al. | |
| 7,024,247 B2 | 4/2006 | Gliner et al. | |
| 7,054,792 B2 | 5/2006 | Frei et al. | |
| 7,058,453 B2 | 6/2006 | Nelson et al. | |
| 7,076,288 B2 | 7/2006 | Skinner | |
| 7,079,977 B2 | 7/2006 | Osorio et al. | |
| 7,134,996 B2 | 11/2006 | Bardy | |
| 7,139,677 B2 | 11/2006 | Hively et al. | |
| 7,146,211 B2 | 12/2006 | Frei et al. | |
| 7,146,217 B2 | 12/2006 | Firlik et al. | |
| 7,146,218 B2 | 12/2006 | Esteller et al. | |
| 7,149,572 B2 | 12/2006 | Frei et al. | |
| 7,164,941 B2 | 1/2007 | Misczynski et al. | |
| 7,167,750 B2 | 1/2007 | Knudson et al. | |
| 7,174,206 B2 | 2/2007 | Frei et al. | |
| 7,177,678 B1 | 2/2007 | Osorio et al. | |
| 7,188,053 B2 | 3/2007 | Nikitin et al. | |
| 7,204,833 B1 | 4/2007 | Osorio et al. | |
| 7,209,786 B2 | 4/2007 | Brockway et al. | |
| 7,209,787 B2 | 4/2007 | DiLorenzo | |
| 7,221,981 B2 | 5/2007 | Gliner | |
| 7,228,167 B2 | 6/2007 | Kara et al. | |
| 7,231,254 B2 | 6/2007 | DiLorenzo | |
| 7,236,830 B2 | 6/2007 | Gliner | |
| 7,236,831 B2 | 6/2007 | Firlik et al. | |
| 7,242,983 B2 | 7/2007 | Frei et al. | |
| 7,242,984 B2 | 7/2007 | DiLorenzo | |
| 7,254,439 B2 | 8/2007 | Misczynski et al. | |
| 7,263,467 B2 | 8/2007 | Sackellares et al. | |
| 7,277,758 B2 | 10/2007 | DiLorenzo | |
| 7,280,867 B2 | 10/2007 | Frei et al. | |
| 7,282,030 B2 | 10/2007 | Frei et al. | |
| 7,289,844 B2 | 10/2007 | Misczynski et al. | |
| 7,292,890 B2 | 11/2007 | Whitehurst et al. | |
| 7,295,881 B2 | 11/2007 | Cohen et al. | |
| 7,299,096 B2 | 11/2007 | Balzer et al. | |
| 7,302,298 B2 | 11/2007 | Lowry et al. | |
| 7,305,268 B2 | 12/2007 | Gliner et al. | |
| 7,321,837 B2 | 1/2008 | Osorio et al. | |
| 7,324,850 B2 | 1/2008 | Persen et al. | |
| 7,324,851 B1 | 1/2008 | DiLorenzo | |
| 7,346,391 B1 | 3/2008 | Osorio et al. | |
| 7,353,063 B2 | 4/2008 | Simms, Jr. | |
| 7,353,064 B2 | 4/2008 | Gliner et al. | |
| 7,373,199 B2 | 5/2008 | Sackellares et al. | |
| 7,389,144 B1 | 6/2008 | Osorio et al. | |
| 7,401,008 B2 | 7/2008 | Frei et al. | |
| 7,403,820 B2 | 7/2008 | DiLorenzo | |
| 7,433,732 B1 | 10/2008 | Carney et al. | |
| 2002/0072782 A1 | 6/2002 | Osorio et al. | |
| 2002/0099417 A1 | 7/2002 | Naritoku et al. | |
| 2002/0103512 A1* | 8/2002 | Echauz et al. | 607/9 |
| 2002/0116030 A1 | 8/2002 | Rezai | |
| 2002/0151939 A1 | 10/2002 | Rezai | |
| 2002/0188214 A1 | 12/2002 | Misczynski et al. | |
| 2003/0074032 A1 | 4/2003 | Gliner | |
| 2003/0083716 A1 | 5/2003 | Nicolelis et al. | |
| 2003/0083726 A1 | 5/2003 | Zeijlemaker et al. | |
| 2003/0125786 A1 | 7/2003 | Gliner et al. | |
| 2003/0130706 A1 | 7/2003 | Sheffield et al. | |
| 2003/0144829 A1 | 7/2003 | Geatz et al. | |
| 2003/0181954 A1 | 9/2003 | Rezai | |
| 2003/0181958 A1 | 9/2003 | Dobak | |
| 2003/0208212 A1 | 11/2003 | Cigaina | |
| 2003/0210147 A1 | 11/2003 | Humbard | |
| 2003/0212440 A1 | 11/2003 | Boveja | |
| 2003/0236558 A1 | 12/2003 | Whitehurst et al. | |
| 2004/0006278 A1 | 1/2004 | Webb et al. | |
| 2004/0088024 A1 | 5/2004 | Firlik et al. | |
| 2004/0122484 A1 | 6/2004 | Hatlestad et al. | |
| 2004/0122485 A1 | 6/2004 | Stahmann et al. | |
| 2004/0133119 A1 | 7/2004 | Osorio et al. | |
| 2004/0138516 A1 | 7/2004 | Osorio et al. | |
| 2004/0138517 A1 | 7/2004 | Osorio et al. | |
| 2004/0138647 A1 | 7/2004 | Osorio et al. | |
| 2004/0138711 A1 | 7/2004 | Osorio et al. | |
| 2004/0147969 A1 | 7/2004 | Mann et al. | |
| 2004/0153129 A1 | 8/2004 | Pless et al. | |
| 2004/0158119 A1 | 8/2004 | Osorio et al. | |
| 2004/0158165 A1 | 8/2004 | Yonce et al. | |
| 2004/0167580 A1 | 8/2004 | Mann et al. | |
| 2004/0172085 A1 | 9/2004 | Knudson et al. | |
| 2004/0172091 A1 | 9/2004 | Rezai | |
| 2004/0172094 A1 | 9/2004 | Cohen et al. | |
| 2004/0176812 A1 | 9/2004 | Knudson et al. | |
| 2004/0176831 A1 | 9/2004 | Gliner et al. | |
| 2004/0199212 A1 | 10/2004 | Fischell et al. | |
| 2004/0249302 A1 | 12/2004 | Donoghue et al. | |
| 2004/0249416 A1 | 12/2004 | Yun et al. | |
| 2005/0004621 A1 | 1/2005 | Boveja et al. | |
| 2005/0020887 A1 | 1/2005 | Goldberg | |
| 2005/0021092 A1 | 1/2005 | Yun et al. | |
| 2005/0021103 A1 | 1/2005 | DiLorenzo | |
| 2005/0021104 A1 | 1/2005 | DiLorenzo | |
| 2005/0021105 A1 | 1/2005 | Firlik et al. | |
| 2005/0021106 A1 | 1/2005 | Firlik et al. | |
| 2005/0021107 A1 | 1/2005 | Firlik et al. | |
| 2005/0021118 A1 | 1/2005 | Genau et al. | |
| 2005/0027284 A1 | 2/2005 | Lozano et al. | |
| 2005/0033378 A1 | 2/2005 | Sheffield et al. | |
| 2005/0033379 A1 | 2/2005 | Lozano et al. | |
| 2005/0038484 A1 | 2/2005 | Knudson et al. | |
| 2005/0049515 A1 | 3/2005 | Misczynski et al. | |
| 2005/0049655 A1 | 3/2005 | Boveja et al. | |
| 2005/0065562 A1 | 3/2005 | Rezai | |
| 2005/0065573 A1 | 3/2005 | Rezai | |
| 2005/0065574 A1 | 3/2005 | Rezai | |
| 2005/0065575 A1 | 3/2005 | Dobak | |
| 2005/0070971 A1 | 3/2005 | Fowler et al. | |
| 2005/0075701 A1 | 4/2005 | Shafer | |
| 2005/0075702 A1 | 4/2005 | Shafer | |
| 2005/0101873 A1 | 5/2005 | Misczynski et al. | |
| 2005/0119703 A1 | 6/2005 | DiLorenzo | |
| 2005/0124901 A1 | 6/2005 | Misczynski et al. | |
| 2005/0131467 A1 | 6/2005 | Boveja et al. | |
| 2005/0131485 A1 | 6/2005 | Knudson et al. | |
| 2005/0131486 A1 | 6/2005 | Boveja et al. | |
| 2005/0131493 A1 | 6/2005 | Boveja et al. | |
| 2005/0143786 A1 | 6/2005 | Boveja et al. | |
| 2005/0148893 A1 | 7/2005 | Misczynski et al. | |
| 2005/0148894 A1 | 7/2005 | Misczynski et al. | |
| 2005/0148895 A1 | 7/2005 | Misczynski et al. | |
| 2005/0153885 A1 | 7/2005 | Yun et al. | |
| 2005/0154425 A1 | 7/2005 | Boveja et al. | |
| 2005/0154426 A1 | 7/2005 | Boveja et al. | |
| 2005/0165458 A1 | 7/2005 | Boveja et al. | |
| 2005/0187590 A1 | 8/2005 | Boveja et al. | |
| 2005/0192644 A1 | 9/2005 | Boveja et al. | |
| 2005/0197590 A1 | 9/2005 | Osorio et al. | |
| 2005/0245971 A1 | 11/2005 | Brockway et al. | |
| 2005/0261542 A1 | 11/2005 | Riehl | |
| 2005/0277998 A1 | 12/2005 | Tracey et al. | |
| 2005/0283200 A1 | 12/2005 | Rezai et al. | |
| 2005/0283201 A1 | 12/2005 | Machado et al. | |
| 2005/0288600 A1 | 12/2005 | Zhang et al. | |
| 2005/0288760 A1 | 12/2005 | Machado et al. | |
| 2006/0009815 A1 | 1/2006 | Boveja | |
| 2006/0074450 A1 | 4/2006 | Boveja | |
| 2006/0079936 A1 | 4/2006 | Boveja | |
| 2006/0094971 A1 | 5/2006 | Drew | |
| 2006/0095081 A1 | 5/2006 | Zhou et al. | |
| 2006/0106430 A1 | 5/2006 | Fowler et al. | |
| 2006/0135877 A1 | 6/2006 | Giftakis et al. | |
| 2006/0135881 A1 | 6/2006 | Giftakis et al. | |
| 2006/0155495 A1 | 7/2006 | Osorio et al. | |
| 2006/0167497 A1 | 7/2006 | Armstrong et al. | |
| 2006/0173493 A1 | 8/2006 | Armstrong et al. | |
| 2006/0173522 A1 | 8/2006 | Osorio | |
| 2006/0190056 A1 | 8/2006 | Fowler et al. | |
| 2006/0195163 A1 | 8/2006 | KenKnight et al. | |
| 2006/0200206 A1 | 9/2006 | Firlik et al. | |
| 2006/0212091 A1 | 9/2006 | Lozano et al. | |
| 2006/0224067 A1 | 10/2006 | Giftakis et al. | |

(56) References Cited

U.S. PATENT DOCUMENTS

| | | |
|---|---|---|
| 2006/0224191 A1 | 10/2006 | DiLorenzo |
| 2006/0241697 A1 | 10/2006 | Libbus et al. |
| 2006/0241725 A1 | 10/2006 | Libbus et al. |
| 2006/0293720 A1 | 12/2006 | DiLorenzo |
| 2007/0027486 A1 | 2/2007 | Armstrong |
| 2007/0027497 A1 | 2/2007 | Parnis |
| 2007/0027498 A1 | 2/2007 | Maschino et al. |
| 2007/0027500 A1 | 2/2007 | Maschino et al. |
| 2007/0032834 A1 | 2/2007 | Gliner et al. |
| 2007/0043392 A1 | 2/2007 | Gliner et al. |
| 2007/0055320 A1 | 3/2007 | Weinand |
| 2007/0073150 A1 | 3/2007 | Gopalsami et al. |
| 2007/0073355 A1 | 3/2007 | DiLorenzo |
| 2007/0088403 A1 | 4/2007 | Wyler et al. |
| 2007/0100278 A1 | 5/2007 | Frei et al. |
| 2007/0100392 A1 | 5/2007 | Maschino et al. |
| 2007/0142862 A1 | 6/2007 | DiLorenzo |
| 2007/0142873 A1 | 6/2007 | Esteller et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0162086 A1 | 7/2007 | DiLorenzo |
| 2007/0167991 A1 | 7/2007 | DiLorenzo |
| 2007/0173901 A1 | 7/2007 | Reeve |
| 2007/0173902 A1 | 7/2007 | Maschino et al. |
| 2007/0179534 A1 | 8/2007 | Firlik et al. |
| 2007/0179557 A1 | 8/2007 | Maschino et al. |
| 2007/0179558 A1 | 8/2007 | Gliner et al. |
| 2007/0208212 A1 | 9/2007 | DiLorenzo |
| 2007/0213785 A1 | 9/2007 | Osorio et al. |
| 2007/0233192 A1 | 10/2007 | Craig |
| 2007/0239210 A1 | 10/2007 | Libbus et al. |
| 2007/0244407 A1 | 10/2007 | Osorio |
| 2007/0249953 A1 | 10/2007 | Frei et al. |
| 2007/0249954 A1 | 10/2007 | Virag et al. |
| 2007/0255147 A1 | 11/2007 | Drew et al. |
| 2007/0255155 A1 | 11/2007 | Drew et al. |
| 2007/0260147 A1 | 11/2007 | Giftakis et al. |
| 2007/0260289 A1 | 11/2007 | Giftakis et al. |
| 2007/0265536 A1 | 11/2007 | Giftakis et al. |
| 2007/0272260 A1 | 11/2007 | Nikitin et al. |
| 2007/0282177 A1 | 12/2007 | Pilz |
| 2008/0033503 A1 | 2/2008 | Fowler et al. |
| 2008/0033508 A1 | 2/2008 | Frei et al. |
| 2008/0046035 A1 | 2/2008 | Fowler et al. |
| 2008/0064934 A1 | 3/2008 | Frei et al. |
| 2008/0071323 A1 | 3/2008 | Lowry et al. |
| 2008/0077028 A1 | 3/2008 | Schaldach et al. |
| 2008/0103548 A1 | 5/2008 | Fowler et al. |
| 2008/0114417 A1 | 5/2008 | Leyde |
| 2008/0119900 A1 | 5/2008 | DiLorenzo |
| 2008/0125820 A1 | 5/2008 | Stahmann et al. |
| 2008/0139870 A1 | 6/2008 | Gliner et al. |
| 2008/0146959 A1 | 6/2008 | Sheffield et al. |
| 2008/0161712 A1 | 7/2008 | Leyde |
| 2008/0161713 A1 | 7/2008 | Leyde et al. |
| 2008/0161879 A1 | 7/2008 | Firlik et al. |
| 2008/0161880 A1 | 7/2008 | Firlik et al. |
| 2008/0161881 A1 | 7/2008 | Firlik et al. |
| 2008/0161882 A1 | 7/2008 | Firlik et al. |
| 2008/0183096 A1 | 7/2008 | Snyder et al. |
| 2008/0183097 A1 | 7/2008 | Leyde et al. |

FOREIGN PATENT DOCUMENTS

| | | |
|---|---|---|
| GB | 2026870 | 2/1980 |
| GB | 2079610 | 1/1982 |
| WO | 2000/064336 | 11/2000 |
| WO | 2004/036377 | 4/2004 |
| WO | 2005/007120 | 1/2005 |
| WO | 2005/053788 | 6/2005 |
| WO | 2005/067599 | 7/2005 |
| WO | 2006/050144 | 5/2006 |
| WO | 2006/122148 | 11/2006 |
| WO | 2007/066343 | 6/2007 |
| WO | 2007/072425 | 6/2007 |
| WO | 2007/124126 | 11/2007 |
| WO | 2007/124190 | 11/2007 |
| WO | 2007/124192 | 11/2007 |
| WO | 2007/142523 | 12/2007 |
| WO | 2008/045597 | 4/2008 |

OTHER PUBLICATIONS

Baevskii, R.M. "*Analysis of Heart Rate Variability in Space Medicine;*" Human Physiology, vol. 28, No. 2, (2002); pp. 202-213.

Baevsky, R.M., et al.; "*Autonomic Cardiovascular and Respiratory Control During Prolonged Spaceflights Aboard the International Space Station;*"J. Applied Physiological, vol. 103, (2007) pp. 156-161.

Boon, P., et al.; "*Vagus Nerve Stimulation for Epilepsy, Clinical Efficacy of Programmed and Magnet Stimulation;*" (2001); pp. 93-98.

Boon, Paul, et al.; "*Programmed and Magnet-Induced Vagus Nerve Stimulation for Refractory Epilepsy;*"Journal of Clinical Neurophysiology vol. 18 No. 5; (2001); pp. 402-407.

Borovikova, L.V., et al.; "*Vagus Nerve Stimulation Attenuates the Systemic Inflammatory Response to Endotoxin;*" Letters to Nature; vol. 405; (May 2000); pp. 458-462.

Brack, Kieran E., et al.; "*Interaction Between Direct Sympathetic and Vagus Nerve Stimulation on Heart Rate in the Isolated Rabbit Heart;*"Experimental Physiology vol. 89, No. 1; pp. 128-139.

Chakravarthy, N., et al.; "*Controlling Synchronization in a Neuron-Level Population Model;*" International Journal of Neural Systems, vol. 17, No. 2 (2007) pp. 123-138.

Clark, K.B., et al.; "*Posttraining Electrical Stimulation of Vagal Afferents with Concomitant Vagal Efferent Inactivation Enhances Memory Storage Processes in the Rat;*" Neurobiology of Learning and Memory, vol. 70, 364-373 (1998) Art. No. NL983863.

Digenarro, Giancarlo et al., "Ictal Heart Rate Increase Precedes EEG Discharge in Drug-Resistant Mesial Temporal Lobe Seizures," Clinical Neurophysiology, No. 115, 2004, pp. 1169-1177.

Frei, M.G., et al.; "Left Vagus Nerve Stimulation with the Neurocybernetic Prosthesis Has Complex Effects on Heart Rate and on Its Variability in Humans:" *Epilepsia*, vol. 42, No. 8 (2001); pp. 1007-1016.

George, M.S., et al.; "*Vagus Nerve Stimulation: A New Tool for Brain Research and Therapy;*"Society of Biological Psychiatry vol. 47 (2000) pp. 287-295.

"*Heart Rate Variability—Standards of Measurement, Physiological Interpretation, and Clinical Use*" Circulation—Electrophysiology vol. 93, No. 5; http://circ.ahajournals.orgicgi/content-nwifull/93/5/1043/F3.

Henry, Thomas R.; "*Therapeutic Mechanisms of Vague Name Stimulation;*". Neurology, vol. 59 (Supp 4) (Sep. 2002), pp. S3-S14.

Hallowitz et al., "*Effects of Vagal Volleys on Units of Intralaminar and Juxtalaminar Thalamic Nuclei in Monkeys;*" Brain Research, vol. 130 (1977), pp. 271-286.

Iasemidis; L.D., et al.; "*Dynamical Resetting of the Human Brain at Epilepctic Seizures: Application of Nonlinear Dynamics and Global Optimization Techniques;*" IEEE Transactions on Biomedical Engineering, vol. 51, No. 3 (Mar. 2004); pp. 493-50.

Iasemidis; L.D., et al.; "*Spatiotemporal Transition to Epileptic Seizures: A Nonlinear Dynamical Analysis of Scalp and Intracranial EEG Recordings;*" Spatiotemporal Models in Biological and Artificial Systems; F.L. Silva et al. (Eds.) IOS Press, 1997; pp. 81-88.

Iasemidis, L.D.; "Epileptic *Seizure Prediction and Control*" IEEE Transactions on Biomedical Engineering, vol. 50, No. 5 (May 2003); pp. 549-558.

Kautzner, J., et al.; "*Utility of Short-Term Heart Rate Variability for Prediction of Sudden Cardiac Death After Acute Myocardial Infarction*" Acta Univ. Palacki. Olomuc., Fac. Med., vol. 141 (1998) pp. 69-73.

Koenig, S.A., et al.; "*Vagus Nerve Stimulation Improves Severely Impaired Heart Rate Variability in a Patient with Lennox-Gastaut-Syndrome*" Seizure (2007) Article in Press—Yseiz-1305; pp. 1-4.

Koo, B., "*EEG Changes With Vagus Nerve Stimulation*" Journal of Clinical Neurophysiology, vol. 18 No. 5 (Sep. 2001); pp. 434-441.

(56) References Cited

OTHER PUBLICATIONS

Krittayaphong, M.D., et al.; "*Heart Rate Variability in Patients with Coronary Artery Disease: Differences in Patients with Higher and Lower Depression Scores*" Psychosomatic Medicine vol. 59 (1997) pp. 231-235.
Leutmezer, F., et al.; "*Electrocardiographic Changes at the Onset of Epileptic Seizures;*" Epilepsia, vol. 44, No. 3; (2003); pp. 348-354.
Lewis, M.E., et al.; "Vagus Nerve Stimulation Decreases Left Ventricular Contractility in Vivo in the Human and Pig Heart" *The Journal of Physiology* vol. 534, No. 2, (2001) pp. 547-552.
Li, M., et al.; "*Vagal Nerve Stimulation Markedly Improves Long-Term Survival After Chronic Heart Failure in Rats;*" Circulation (Jan. 2004) pp. 120-124.
Licht, C.M.M.; *Association Between Major Depressive Disorder and Heart Rate Variability in the Netherlands Study of Depression and Anxiety (Nesda)*; Arch. Gen Psychiatry, vol. 65, No. 12 (Dec. 2008); pp. 1358-1367.
Lockard et al., "*Feasibility and Safety of Vagal Stimulation in Monkey Model;*" Epilepsia, vol. 31 (Supp. 2) (1990), pp. S20-S26.
Long, Teresa J. et al., "Effectiveness of Heart Rate Seizure Detection Compared to EEG in an Epilepsy MoitoringUnit (EMU)," abstract of AES Proceedings, Epilepsia, vol. 40, Suppl. 7, 1999, p. 174.
McClintock, P., "*Can Noise Actually Boost Brain Power*" Physics World Jul. 2002; pp. 20-21.
Mori, T., et al.; "*Noise-Induced Entrainment and Stochastic Resonance in Human Brain Waves*" Physical Review Letters vol. 88, No. 21 (2002); pp. 218101-1-218101-4.
Mormann, F., "Seizure prediction: the long and winding road," Brain 130 (2007), 314-333.
Nouri, M.D.; "*Epilepsy and the Autonomic Nervous System*" emedicine (updated May 5, 2006); pp. 1-14; http://www.emedicine.com/neuro/topic658.htm.
O'Donovan, Cormac A. et al., "Computerized Seizure Detection Based on Heart Rate Changes," abstract of AES Proceedings, Epilepsia, vol. 36, Suppl. 4, 1995, p. 7.
O'Regan, M.E., et al.; "*Abnormalities in Cardiac and Respiratory Function Observed During Seizures in Childhood*" Developmental Medicine & Child Neurlogy, vol. 47 (2005) pp. 4-9.
Osorio, Ivan et al., "An Introduction to Contingent (Closed-Loop) Brain Electrical Stimulation for Seizure Blockage, to Ultra-Short-Term Clinical Trials, and to Multidimensional Statistical Analysis of Therapeutic Efficacy," Journal of Clinical Neurophysiology, vol. 18, No. 6, pp. 533-544, 2001.
Osorio, Ivan et al., "Automated Seizure Abaatement in Humans Using Electrical Stimulation," Annals of Neurology, vol. 57, No. 2, pp. 258-268, 2005.
Pathwardhan, R.V., et al., Control of Refractory status epilepticus precipitated by anticonvulasnt withdrawal using left vagal nerve stimulation: a case report, Surgical Neurology 64 (2005) 170-73.
Poddubnaya, E.P., "Complex Estimation of Adaptation Abilities of the Organism in Children Using the Indices of Responsiveness of the Cardiovascular System and Characteristics of EEG" *Neurophysiology* vol. 38, No. 1 (2006); pp. 63-74.
Robinson, Stephen E et al., "Heart Rate Variability Changes As Predictor of Response to Vagal Nerve Stimulation Therapy for Epilepsy," abstract of AES Proceedings,Epilepsia, vol. 40, Suppl. 7, 1999, p. 147.
Rugg-Gunn, F.J., et al.; "*Cardiac Arrhythmias in Focal Epilepsy: a Prospective Long-Term Study*" www.thelancet.com vol. 364 (2004) pp. 2212-2219.
Sajadieh, A., et al.; "*Increased Heart Rate and Reduced Heart-Rte Variability are Associated with Subclinical Inflammation in Middle-Aged and Elderly Subjects with No Apparent Heart Disease*" European Heart Journal vol. 25, (2004); pp. 363-370.
Schernthaner, C., et al.; "*Autonomic Epilepsy—The Influence of Epileptic Discharges on Heart Rate and Rhythm*" The Middle European Joural of Medicine vol. 111, No. 10 (1999) pp. 392-401.
Sunderam, Sridhar et al., "Vagal and Sciatic Nerve Stimulation Have Complex, Time-Dependent Effects on Chemically-Induced Seizures: A Controlled Study," Brain Research, vol. 918, pp. 60-66, 2001.
Terry et al.; "*The Implantable Neurocybernetic Prosthesis System*", Pacing and Clinical Electrophysiology, vol. 14, No. 1 (Jan. 1991), pp. 86-93.
Tubbs, R.S., et al.; "*Left-Sided Vagus Nerve Stimulation Decreases Intracranial Pressure Without Resultant Bradycardia in the Pig: A Potential Therapeutic Modality for Humans*" Child's Nervous System Original Paper; Springer-Verlag 2004.
Umetani, M.D., et al.; "*Twenty-Four Hour Time Domain Heart Rate Variability and Heart Rate: Relations to Age and Gender Over Nince Decades*" JACC vol. 31, No. 3; (Mar. 1998); pp. 593-601.
Van Elmpt, W.J.C., et al.; "*A Model of Heart Rate Changes to Detect Seizures in Severe Epilepsy*" Seizure vol. 15, (2006) pp. 366-375.
Vonck, K., et al. "*The Mechanism of Action of Vagus Nerve Stimulation for Refractory Epilepsy—The Current Status*", Journal of Neurophysiology, vol. 18 No. 5 (2001), pp. 394-401.
Weil, Sabine et al, "Heart Rate Increase in Otherwise Sublinical Seizures Is Different in Temporal Versus Extratemporal Seizure Onset: Support for Temporal Lobe Automatic Influence," Epileptic Disord., vol. 7, No. 3, Sep. 2005, pp. 199-204.
Woodbury, et al., "*Vagal Stimulation Reduces the Severity of Maximal Electroshock Seizures in Intact Rats. Use of a Cuff Electrode for Stimulating and Recording*"; Pacing and Clinical Electrophysiology, vol. 14 (Jan. 1991), pp. 94-107.
Zabara, J.; "*Neuroinhibition of Xylaine Induced Emesis*" Pharmacology & Toxicology, vol. 63 (1988) pp. 70-74.
Zabara, J. "*Inhibition of Experimental Seizures in Canines by Repetivie Vagal Stimulation*" Epilepsia vol. 33, No. 6 (1992); pp. 1005-1012.
Zabara, J., et al.; "*Neural Control of Circulation I*"The Physiologist, vol. 28 No. 4 (1985); 1 page.
Zabara, J., et al.; "*Neuroinhibition in the Regulation of Emesis*" Space Life Sciences, vol. 3 (1972) pp. 282-292.
Zijlmans, Maeike et al., "Heart Rate Changes and ECG Abnormalities During Epileptic Seizures: Prevalence and Definition of an Objective Clinical Sign," Epilepsia, vol. 43, No. 8, 2002, pp. 847-854.

\* cited by examiner

METHOD AND SYSTEM FOR LOGGING QUANTITATIVE SEIZURE INFORMATION AND ASSESSING EFFICACY OF THERAPY USING CARDIAC SIGNALS

CROSS REFERENCE TO RELATED APPLICATIONS

This patent application is a divisional of U.S. patent application Ser. No. 10/997,540, filed Nov. 24, 2004 now U.S. Pat. No. 9,050,469, which claims priority of Provisional Patent Application No. 60/525,501 entitled "A Method and Apparatus for Logging, Warning and Treatment of Seizures Using Cardiac Signals," filed Nov. 26, 2003, which are incorporated herein by reference in their entirety.

BACKGROUND OF THE INVENTION

1. Field of the Invention

The present invention relates to medical devices and, more specifically without limitation, to implanted medical devices.

2. Description of the Related Art

Epilepsy affects about 2.3 million Americans, and its direct and indirect annual costs amount to approximately $12.5 billion. Although anti-epileptic drugs are useful, 20-30% of persons are not helped by them and up to 30% of those treated have intolerable or serious side effects.

Recently published studies demonstrate the importance of quantitative analysis of brain signals for automated warning and blockage of seizures, optimization of existing therapies and development of new ones. Cardiac activity is under cerebral control. That is, certain changes in global, regional or focal brain activity, either physiological or pathological, modify heart activity. Epileptic seizures are one of the pathological brain states associated with changes in heart activity including but not limited to changes in heart rate, most frequently an increase and referred to as ictal tachycardia, or in other indices of cardiac function such as R-R variability. The incidence of heart changes increases as the seizure spreads outside its site of origin to other brain regions being, for example invariably present in all subjects with primarily or secondarily generalized tonic-clonic seizures ("convulsions"), in whom purportedly, most or all of the brain is involved. These changes reflect shifts in the ongoing interplay between sympathetic and parasympathetic influences, which can be quantified using time or frequency domain methods of analysis. For example, tachycardia precedes electrographic onset of temporal lobe seizures by several seconds, as ascertained via scalp electrodes (EEG), while combined activation of parasympathetic and sympathetic systems as estimated by using spectral analysis of oscillations in R-R intervals at respiratory and non-respiratory frequencies, may be detectable minutes in advance of seizure onset. Since these changes may precede visible electrographic or behavioral manifestations indicative of seizures and even of the so-called "aura," they may have predictive value. Real-time prediction or detection of epileptic seizures, based on extracerebral sources such as the heart, is of great clinical and practical value as it obviates the reliance on cerebral signals which are highly complex and of high dimensionality and whose origin may not only be difficult to localize but quite often requires invasive intracranial implantation of electrodes or other sensors.

While methods presently exist to detect seizures using cardiac signals and quantify their characteristics, for example as described in U.S. Pat. No. 6,341,236 which is incorporated herein by reference in its entirety, no system for logging the times of seizures and their quantitative characteristics, such as date and time of occurrence, and duration based on the degree of cardiac changes, and for using this information in the objective assessment of seizure frequency and of therapeutic intervention, presently exists. This is partially due to the impact of artifacts (noise) on EKG signal analysis which can lead to inaccuracies in heart rate assessments.

Thus, the need exists for a system and method for logging seizures, or other events originating in the brain that impact cardiac activity, and associated event characteristics such as frequency, duration, intensity, and severity. Moreover, this system and method needs to be robust in the presence of artifacts or other sources of noise. The need also exists for a minimally invasive system and method to provide effective and objective means for assessing the efficacy of therapies used to control seizures.

SUMMARY OF THE INVENTION

Changes in heart activity associated with seizures can be used to automatically and in real-time detect the seizures, quantify their frequency, duration, intensity, or severity as reflected in the cardiac signal changes, predict their electrographic or clinical onset in a subset of cases, and control the seizures via therapeutic intervention. The present invention enables the logging of this information and its utilization to objectively assess the efficacy of an applied therapy. To accomplish this task with improved robustness in the presence of signal artifacts or noise, the invention can utilize EKG and complementary information obtained from other signals representative of cardiac function such as the phonocardiogram (PKG), echocardiogram, or ultrasound.

BRIEF DESCRIPTION OF THE DRAWING FIGURES

DETAILED DESCRIPTION OF THE PREFERRED EMBODIMENTS

Figure 1:
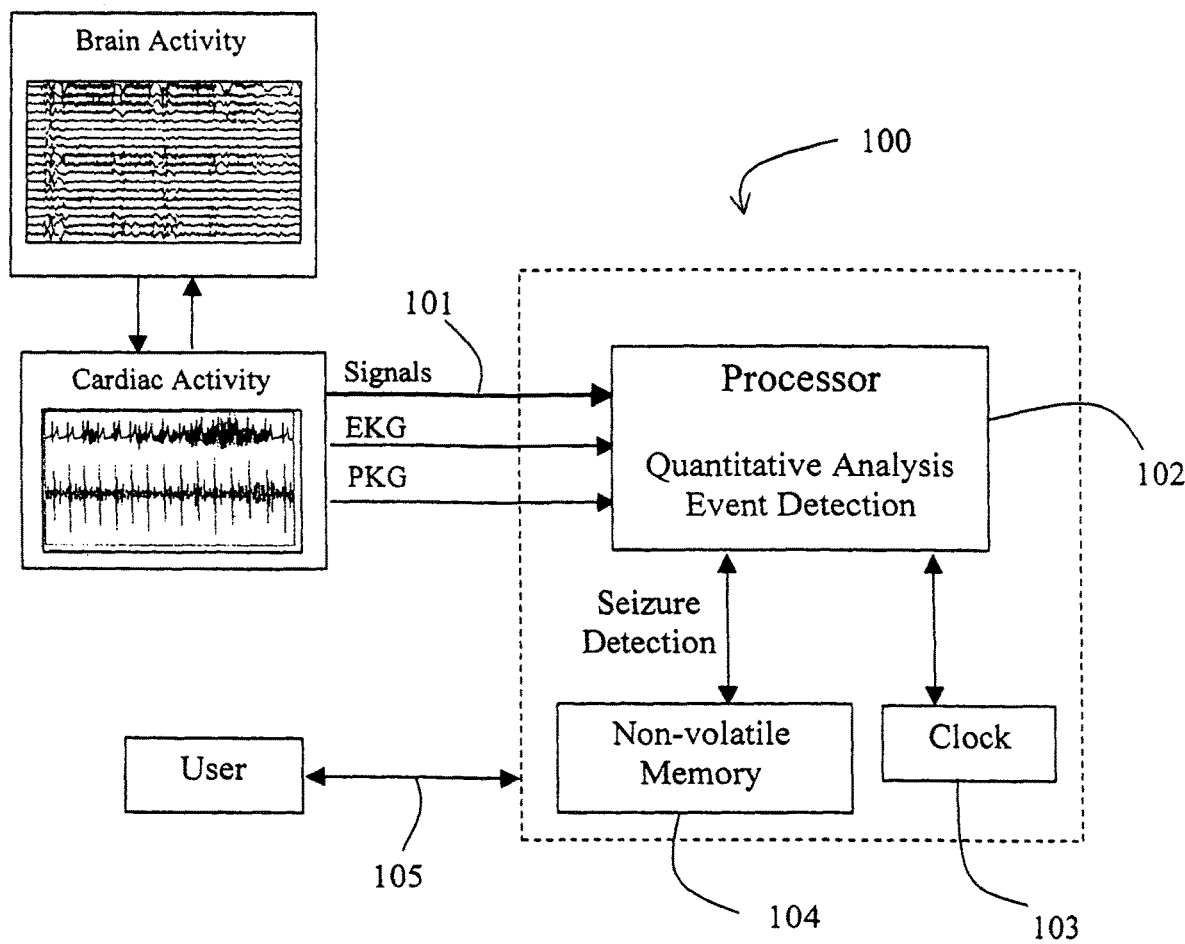
FIG. 1 is a schematic representation of a system for receiving and analyzing cardiac signals and detecting and logging seizures according to the present invention.

Changes in certain types of global, regional or focal brain activity, either physiological or pathological, modify heart activity. Epileptic seizures are one important example of a pathological brain state with demonstrated association to changes in heart activity. The incidence of heart changes increases as the seizure spreads outside its site of origin to other brain regions being, for example invariably present in all subjects with primarily or secondarily generalized tonic-clonic seizures ("convulsions"), in whom purportedly, most or all of the brain is involved. Real-time prediction or detection, and quantitative analysis of epileptic seizures, based on extracerebral sources such as the heart, is of great clinical and practical value as it obviates the reliance on cerebral signals which are highly complex and of high dimensionality, and whose origin may not only be difficult to localize but quite often requires invasive intracranial implantation of electrodes or other sensors. The invention disclosed herein, and depicted schematically in FIG. 1, utilizes information present in signals 101 representative of the cardiac activity state, fed to system 100 that performs real-time quantitative analysis of this information in a processor 102. This processor analyzes and measures relevant changes in the cardiac activity state in order to predict or detect and quantify underlying events occurring in the brain of a subject. The system is configured to include a clock 103 and non-volatile memory 104 to enable these events and relevant data and information about associated event features to be logged. These features may include, but are not limited to, start time, end time, or duration of detected cardiac changes which provide information about underlying seizures or other brain events, the frequency or relative intensity of these changes, and the evolution of the distribution of such features as interbeat intervals. These and other features representative of cardiac state well known to one skilled in the art, such as heart rate and heart rate variability measures, can be measured and relevant changes logged. The system can be configured with a communication interface 105 that allows the subject or other user to access information from the logs stored in non-volatile memory 104 and/or to program parameters used in the operation of the system 100, including parameters involved in the analysis of cardiac signals performed using processor 102.

While methods presently exist to detect seizures using cardiac signals and quantify their characteristics, for example as described in U.S. Pat. No. 6,341,236, no system presently exists for logging these quantitative characteristics, such as times of occurrence, durations and degrees of cardiac changes associated with seizures or other underlying brain events and for using this information in objective assessment of the neurological disorder and of efficacy of therapeutic intervention. This is partially due to the impact of artifacts (noise) on EKG signal analysis which can lead to inaccuracies in heart rate assessments.

Figure 2:
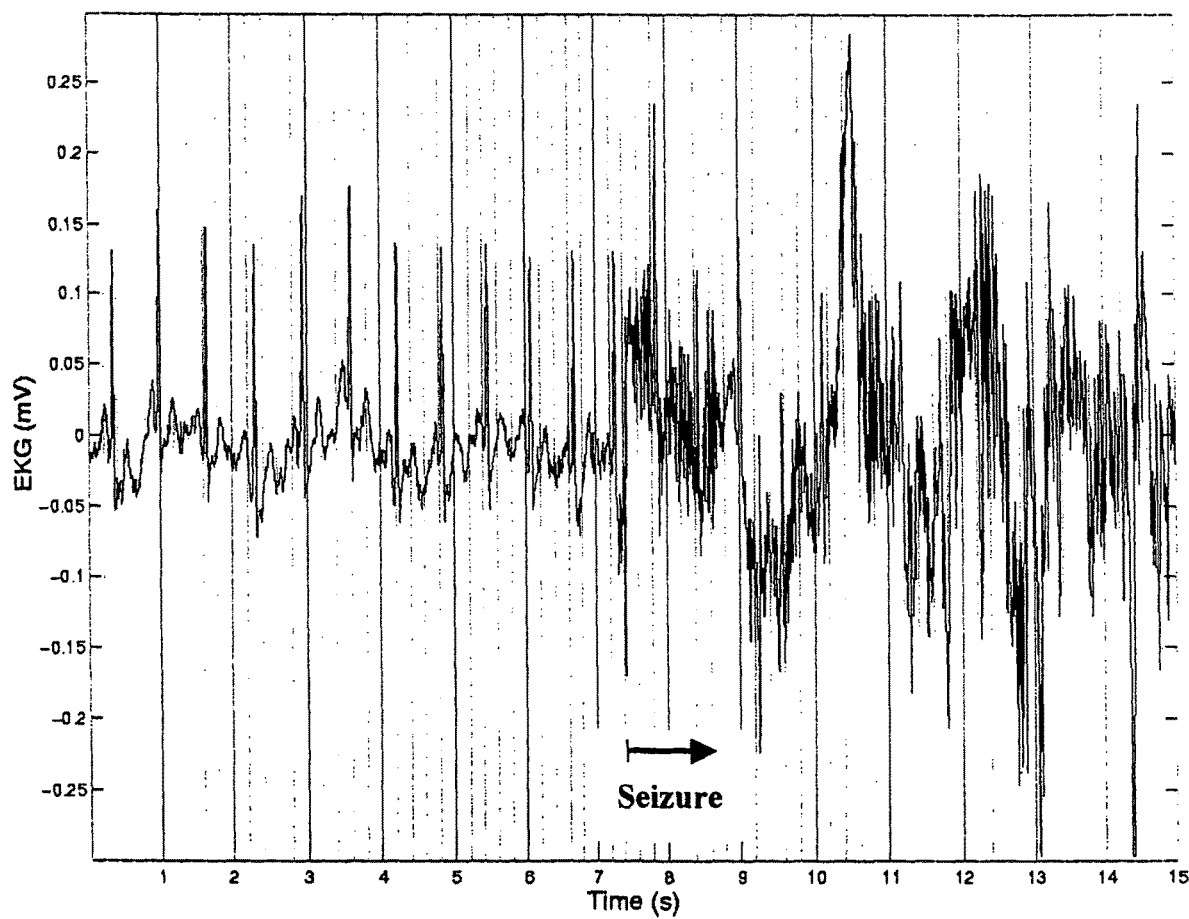
FIG. 2 shows an EKG signal corrupted by artifact at the start of a seizure.
Figure 3:
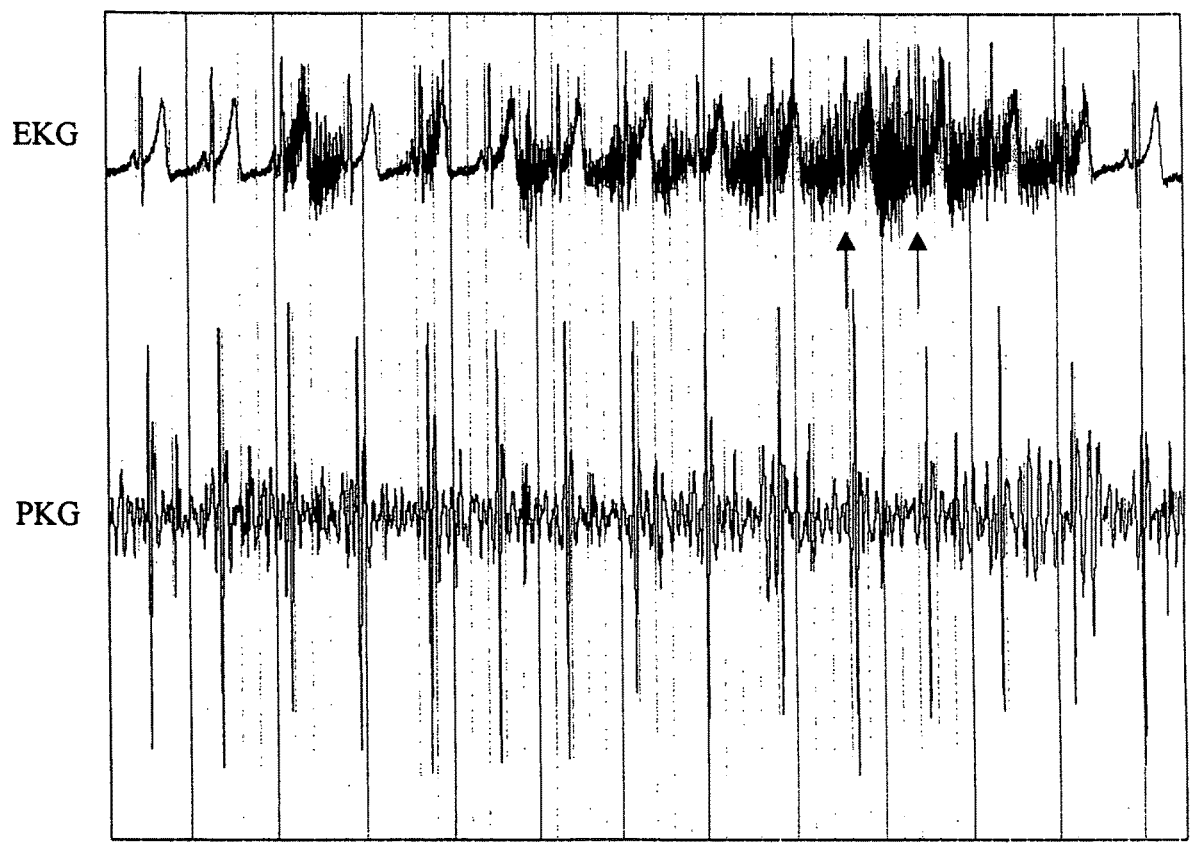
FIG. 3 illustrates simultaneously recorded EKG and PKG data and the ability of PKG to provide complementary information regarding cardiac function contained therein.

Seizures often are associated with movement, muscle, and other artifacts that can obscure or distort the EKG making it difficult or impossible to extract the important information contained in the contaminated signals. FIG. 2 illustrates an EKG signal from a subject just before and during the onset of an epileptic seizure in which there is significant artifact present as the seizure begins. This artifact makes it difficult to determine from this signal precisely when heart beats are occurring. One strategy to overcome noise is to simultaneously acquire other cardiac signals such as PKG to take advantage of the fact that these other signals have different sensitivities than EKG to certain types of noise. This approach increases the information content about the state of the heart, and indirectly about the state of the brain, and decreases the probability of signal loss or degradation by noise. FIG. 3 illustrates the differential sensitivity to noise: the EKG signal shown is contaminated by muscle artifact, a common source of noise during seizures, and is not easily recognizable visually or using spectral signal analysis while the simultaneously recorded PKG is virtually immune to this type of noise. The two arrows in FIG. 3 annotate time points when R-waves in the EKG are obscured by muscle artifacts; FIG. 3 also displays the simultaneously recorded PKG signal which is immune to this type of artifacts.

The PKG can be used instead of EKG for tracking heart rate and its variability given the high temporal correlation between the S1 and the QRS complex. Simultaneous use of PKG and EKG allows the system access to good quality information for more complete and accurate tracking of the cardiac system dynamics and, indirectly, of brain dynamics effecting the heart. Those skilled in the art can appreciate that many other types of physical or chemical heart signals suitable for use with implantable devices can also be used in addition to, or instead of, EKG and PKG for this purpose.

In view of the clinical importance of real-time automated quantitative seizure analysis and the greater signal-to-noise ratio and shorter propagation time from source to sensor, and ease of use of heart signals (electrocardiogram, EKG, or phonocardiogram, PKG) compared to scalp signals (EEG) or intracranial recording of electrical signals (ECoG), the approach of the present invention disclosed herein makes use of these signals for a) the invasive or non-invasive extracerebral, real-time automated detection of seizures based on heart signals; b) the logging of frequency, date/time of occurrence, relative intensity and relative duration of seizures; c) the anticipation of electrographic or behavioral seizure onset and/or loss of function in a subgroup of subjects with epilepsy, for automated warning and other useful purposes; and d) the automated delivery of a selected therapy, either contingent or closed-loop. Additionally and of equal importance is the ability to detect, in real-time, cardiac rhythm abnormalities, which may be life-threatening and which are temporally correlated with seizures or occur in between seizures and to provide appropriate intervention such as pacing or defibrillation.

Use of cardiac signals such as EKG and/or PKG for the automated detection of seizures, and in certain cases for the anticipation of their onset, will complement and, in a subgroup of subjects with pharmaco-resistant epilepsy, may replace scalp or intracranial (invasive) acquisition of cortical signals for automated warning and/or therapy delivery and in either case will allow for seizure logging and other tasks. One of the main advantages of using EKG/PKG for seizure detection is that unlike methods based on cortical signals recorded either directly from the cortex, which requires a craniotomy or burr hole, or indirectly from the scalp (EEG), it is not critically, dependent on accurate placement of electrodes and, in a subset of cases, the onset of heart changes may even precede scalp or behavioral changes providing yet another advantage.

Heart signals, can be obtained from several body sites obviating, in a subgroup of patients, the need for surgery, thus decreasing the inconvenience, stress, cost, potential morbidity and recovery time associated with such procedures. Furthermore, the wealth of commercially available, low power, implantable devices for analysis and control of heart signals can be easily leveraged for this application. Another advantage of EKG over EEG or ECoG is its lower dimensionality and relative simplicity wherein a single channel recording is sufficient for capturing all of the information necessary for the tasks at hand.

Those skilled in the art can appreciate that in certain cases or situations, dual, simultaneous monitoring of brain and heart may be necessary or useful to improve detection of changes in either organ or to improve the efficacy of control measures. Also, undesirable changes in heart activity caused by abnormal brain activity may be better controlled by directing the intervention to the brain rather than to the heart. For instance, while asystole caused by seizures can be controlled using a demand pacemaker, a more definitive and rational approach is to prevent or block asystole-inducing seizures. It is clear that the dynamic interactions between heart and brain can be exploited to detect changes and to control them by monitoring either organ or both and by applying control to either of them, or to both.

Frei and Osorio and others, see for example U.S. Pat. No. 6,341,236, have disclosed methods for automated EKG analysis and detection of cardiac signal changes associated with epileptic seizures. The methods developed by Frei and Osorio are especially well-suited for seizure detection using heart signals, a task which requires analysis of data over very short windows (1-2 sec). The length requirements of other methods for standard low/ultra-low frequency band power assessments of heart rate variability, typically five-minute segments assumed to be stationary, are much longer than the duration of a seizure or a dangerous cardiac abnormality that may lead to sudden death. In addition, the assumptions regarding stationarity of the system/signal are counter to the well-known nonstationarity of the normal cardiac system. Given these deficiencies, it is therefore impractical to apply methods of heart signal analysis that require long segments of data, minutes for example, for the detection of phenomena for which warning and control must take place in a very short time period (e.g., under ten seconds) for purposes of safety and efficacy. Another advantage of the methods of the present invention is that they can be used to quantify the intensity, type, and evolution of cardiac changes, which in turn may be used to detect and estimate the duration and intensity of underlying brain state changes whether physiological or pathological. The changes in heart activity that may indicate a possible onset of a seizure (a pathologic state change) include, but are not limited to, changes in heart rate and heart rate variability and their interrelationship, rhythm, morphology of the P-QRS-T complex or of the length of the different intervals (e.g., Q-T).

One skilled in the art can appreciate that, in addition to the aforementioned methods, a number of methods for detection and analysis of cardiac signal changes exist in prior art, many of which have been implemented in hardware, software, or in a hybrid configuration, and which can be used, for example, to obtain the time of each heart beat as well as the interbeat (e.g., R-R) interval. One skilled in the art will appreciate for example, that the R-R interval times or other quantities representative of cardiac state may be processed/analyzed using methods in the time or frequency domains to generate a multitude of derivative signals/sequences or ratios from which a wealth of information can be obtained about the heart, including instantaneous heart rate (IHR), its average rate in fixed or moving windows of any desired length, and measures of heart rate variability ("HRV") (e.g., standard deviation of means of R-R intervals in a moving window, or the second derivative of instantaneous heart rate, etc.) on any desired timescale but with emphasis on those timescales suitable for seizure detection. Changes in the distributions of these, or any other quantity derived from the time-of-beat sequence, as time evolves can be detected and quantified in real-time, for example using the "lambda estimator" as disclosed in Nikitin et al, U.S. Patent Application Publication No. 20030187621, or other statistical methods. Stereotypical patterns, if found in these data, may be learned over time as more seizures are recorded and analyzed. For example, cardiac data from a subject can be used to establish normal or baseline patterns for this subject and compared against moving windows of new data to determine deviations from normalcy or baseline, proximity to dangerous or undesirable patterns, and to quantify these deviations. Degree of absolute or relative changes in heart rate, heart rate variability, and their interrelationship, ST-wave depression, and QT prolongation are examples of such quantities. The time of specific changes and their duration and/or intensity are obtainable from these analyses. As in the aforementioned Nikitin et al reference, one skilled in the art will appreciate that the analysis of interest can be multifactorial and/or multidimensional. For example, U.S. Pat. No. 6,341,236 of Osorio and Frei disclosed that changes in the relationship between IHR and HRV provide information about heart function which is not obtainable if IHR and HRV are analyzed separately.

The aforementioned lambda estimator provides one of many possible examples illustrating how statistical changes in feature signals, even when multi-dimensional, obtained from cardiac recordings, such as EKG, can be quantified as they evolve. By applying thresholding techniques or, more generally, by identifying values of quantified features that are associated with particular cardiac or body states, e.g., seizures, the start and end of these state changes can be localized in time and their relative intensity quantified.

These analyses may also be applied to PKG signals in order to detect similar, complementary, or different changes reflective of heart state. Other measures that may be used by the present invention include but are not limited to: duration including time of onset and termination of changes in heart rate or in any of its derivatives; changes in heart rate variability or in any of its derivatives; changes in rhythmicity or in generation and conduction of electrical impulses; or changes in the acoustic properties of heart beats and their variability. It will be appreciated that additional information may be obtained through analysis of occurrence times of other EKG waveforms such as Q-T intervals, changes in spectral properties of the EKG or signal morphology, as well as time-of-beat information obtained from PKG such as s1-s1 intervals, amplitude (magnitude) of the signal, or changes in its waveshape and/or spectral characteristics, etc. For example, changes in the magnitude or rate of change of the high- and low-frequency components of the heart beat, using autoregressive, Fast Fourier, wavelets, Intrinsic Timescale Decomposition (U.S. patent application Ser. No. 10/684,189, filed Oct. 10, 2003), or other suitable techniques, may be used alone or combined with other cardiac measures to increase the sensitivity, specificity, and/or speed of prediction or detection of seizures or in their ability to quantify brain state changes. Other measures derived from the raw or processed signals that may be of additional use in the present invention include, but are not limited to, analysis of entropy, correlation dimension, Lyapunov exponents, measures of synchronization, fractal analysis, etc.

The real-time prediction, detection and quantification of seizures that is possible by using the methods disclosed herein and/or associated systems may be adapted or tailored to fit an individual's cardiac state change patterns or characteristics, thereby increasing sensitivity, specificity or speed of detection of state changes. The performance of the detection methods, such as sensitivity, specificity and speed, may be enhanced, if necessary, by characterizing baseline patterns for a subject and comparing them against moving windows of current data to determine and quantify deviations from baseline and proximity to patterns indicative of state change. These can be used, together with the frequency, intensity, and duration of heart signal changes, time to maximal deviation from baseline, time to recovery to baseline rates, for assessing a patient's condition, safety risks, and even efficacy of therapy. Moreover, degree of conformance to stereotypical cardiac signal patterns that may be associated with certain seizure types can be used to infer other severity-related measures such as degree of seizure spread in the brain. Simultaneous recording and analysis of other non-cardiac signals, such as muscle, joints, skin or peripheral nerves, may also improve prediction, detection and quantification of state changes. For example, the recording, analysis, and comparison of changes in cardiac signals during the state change of interest, e.g., seizures, to that obtained during activities such as exercise, can increase their sensitivity, specificity, and/or detection speed for real-time seizure detection purposes, or for detecting changes of body state. These processes may be carried out on- or off-line.

The information about heart state provided by the present invention can be used to compute seizure index, which is defined as the fraction of time spent in a seizure over a moving window of a given size. The information can also be used to determine seizure severity, e.g., using the product of intensity and duration. These and other measures may be logged as part of the present invention (or later computed from other logged information) and can provide valuable diagnostic and prognostic information, as well as information regarding efficacy of any therapy attempted during the period of monitoring/analysis. The set of logged information stored by the present invention can also be used to develop models that may allow or refine seizure prediction or detection (using cardiac signals or in general) and shed light on an individual's seizure dynamics.

The implantable or portable device implementing the present invention is configured to include a real-time clock and a rewritable, non-volatile memory, as well as one or more sensors for use in recording EKG, PKG and/or other representative signals indicative of cardiac function and/or state, such as echocardiogram, ultrasound, blood pressure, blood flow rate or volume, heart muscle tension, etc., and processing components capable of receiving, conditioning, and analyzing the EKG and/or PKG signals to detect and/or quantify events of interest such as seizures. The logging process consists of reading the real-time clock each time an event or cluster of events of a certain designated type occurs, and logging the clock time and variables associated with the quantification of the event to the non-volatile memory. These variables may include but are not limited to information obtained through processing of the signals, and/or the raw signals themselves, i.e., "loop recordings" of events.

The system of the present invention may be further configured with an output mechanism to: a) warn the subject of an impending seizure or other type of detected event such as a cardiac arrhythmia, low system battery, full memory, etc., and b) deliver a selected therapy to the subject when heart activity reaches or exceeds safe or prespecified limits. For example, Osorio and Frei in U.S. Pat. No. 6,341,236 disclose a means to trigger the pacing of the heart in the event of a seizure detected by analysis of EKG. Osorio et al., in U.S. Pat. No. 5,995,868, disclose a method of treating seizures by, among other methods, stimulating the brain, heart and/or vagus nerve when a seizure is detected. The output mechanism may include or be connected to a neurostimulator and/or a pacemaker to control brain and/or heart activity within prespecified tolerable/safe limits. Commonly used types of warnings include audio alarms with varied tones and/or combinations of short and long sounds, other types of acoustic devices, LED or other visual displays, e.g., flashing lights, etc., low-voltage so-called "tickler" stimulus, and communication with external devices, e.g., triggering an external device such as "calling 911," etc.

Any additional implanted or portable device may also use the non-volatile memory for storing information about events through the use of a uni- or bi-directional communications protocol. For example, a pacemaker that detects an unusual EKG rhythm or heart beat pattern could trigger the device described herein that an event has occurred and potentially could communicate other features/attributes of the event, such as type, severity, etc., to the device for logging purposes. The system may also contain a display, or means to be externally interrogated, to review and/or download the information it has stored and/or logged for review by the user, subject, or physician. In addition to logging seizures or other events of neurological origin which impact the cardiac system, the system and method of the present invention can be used to objectively assess the efficacy of therapies used to control the occurrence or severity of these events. For example, when a subject takes medication in order to control his seizures, the availability of a seizure log that includes their time of occurrence, severity, and other features can be analyzed in reference to administration times and concentrations of medication or other therapy, which also can be logged by the system via the communication interface described above. Such comparisons enable the modeling and objective efficacy assessment of the effect of the therapy on the system. For instance, the seizure frequency measure plotted against the level of medication expected to be present in the subject's system as time evolves allows the user to optimize dosing levels and times to minimize seizure frequency.

Therapies administered to the subject based on the cardiac signal change may also include administration of a drug or medicament, features of which may include medicament type, dose, administration site, time of delivery, duration of delivery, rate of delivery, frequency of delivery, and inter-delivery interval. Therapies administered to the subject based on the cardiac signal change may include thermal regulation of the brain, features of which may include time of delivery, duration of delivery, rate of delivery, frequency of delivery, inter-delivery interval, administration site, intensity of therapy, and size of region affected by thermal regulation.

It is to be understood that while certain forms of the present invention have been illustrated and described herein, it is not to be limited to the specific forms or arrangement of parts described and shown.

What is claimed and desired to be covered by Letters Patent is as follows:

1. A method of detecting and logging an epileptic seizure event via a medical system, comprising:
   receiving a cardiac signal of a patient into a processor of the medical system;
   determining via the processor of the medical system a cardiac signal change based on the received cardiac signal;
   detecting via the processor of the medical system an onset of an epileptic seizure based on the cardiac signal change;
   determining via the processor of the medical system an epileptic seizure characteristic where the epileptic seizure characteristic is an intensity, a duration, a date and a time of an occurrence of the epileptic seizure;
   logging the epileptic seizure characteristic in a memory;
   transferring to an external device the logged epileptic seizure characteristic; and
   delivering a therapy based on a determination of the onset of the epileptic seizure;
   wherein the therapy to treat the epileptic seizure utilizes stimulating a region of a brain of the patient via a first electrical signal and stimulating a vagus nerve via a second electrical signal.

2. The method of claim 1, further comprising determining one or more stereotypical patterns based on one or more epileptic seizure occurrences.

3. The method of claim 2, further comprising detecting the onset of the epileptic seizure based on the one or more stereotypical patterns.

4. The method of claim 1, further comprising providing a warning signal.

5. The method of claim 1, further comprising determining an epileptic seizure index.

\* \* \* \* \*